United States Patent [19]

Kuisma et al.

[11] Patent Number: 4,500,940
[45] Date of Patent: Feb. 19, 1985

[54] CAPACITIVE HUMIDITY SENSOR AND METHOD FOR THE MANUFACTURE OF SAME

[75] Inventors: Heikki T. Kuisma; Ari Lehto, both of Helsinki; Jouko S. Jalava, Vantaa, all of Finland

[73] Assignee: Vaisala Oy, Helsinki, Finland

[21] Appl. No.: 562,746

[22] Filed: Dec. 19, 1983

[30] Foreign Application Priority Data

Dec. 21, 1982 [FI] Finland .................................. 824392

[51] Int. Cl.³ .............................................. H01G 5/20
[52] U.S. Cl. .................................... 361/286; 73/336.5
[58] Field of Search .......................... 361/286; 338/35; 174/52 FP; 73/335, 336, 336.5

[56] References Cited

U.S. PATENT DOCUMENTS

| | | | |
|---|---|---|---|
| 3,397,278 | 8/1968 | Pomerantz | 174/52 FP |
| 3,983,527 | 9/1976 | Ohsato et al. | 338/35 |
| 4,167,725 | 9/1979 | Shimizu et al. | 338/35 |

Primary Examiner—Donald A. Griffin
Attorney, Agent, or Firm—Birch, Stewart, Kolasch & Birch

[57] ABSTRACT

The present publication describes a capacitive humidity sensor and a method for the manufacture of same. The sensor comprises a substrate (1), first (5) and second bottom electrodes (4), which have been fitted close to each other on the substrate (1), an active layer (7), which fills the area between the first (5) and the second bottom electrodes (4) on the substrate (1) and extends to above the top face of the second electrode (4). According to the invention, the sensor further consists of structures (6) connected to the top face of the first electrode (5), made of a conductive material, and being beam-shaped with an upwardly widening section and being placed side by side, the said structures (6) limiting portions (7) of the active layer between themselves from two sides, and a narrow slot (26) being provided between the top faces of the said structures. Owing to its construction, the sensor is not sensitive to touching.

6 Claims, 13 Drawing Figures

CAPACITIVE HUMIDITY SENSOR AND METHOD FOR THE MANUFACTURE OF SAME

The present invention is concerned with a capacitive humidity sensor.

BACKGROUND OF THE INVENTION

The invention is also concerned with a method for the manufacture of such a humidity sensor.

FIGS. 1 and 2 show the cross-sections of two capacitive humidity sensors of types known in the prior art. In the construction in accordance with FIG. 1, there are two bottom electrodes 2 between the substrate 1 and the isolation layer 15. In addition to the parts of the above construction, the construction of FIG. 2 also includes a surface electrode 3 placed on top of the isolation layer 15.

As a rule, the electrode structure of a capacitive humidity sensor must meet, e.g., the following requirements:

(a) humidity must have unhindered access of penetration into the isolation material,
(b) the electrodes must be electrically well conductive and mechanically durable, and
(c) the electric field between the electrodes must not penetrate onto the sensor surface, where there may be electrically conductive impurities.

The construction of FIG. 1 meets the requirements a and b, but not the requirement c. The construction of FIG. 2, on the other hand, meets the requirement c, but the requirements a and b substantially exclude each other.

As regards the state of prior-art technology, reference should be made in particular to the following publications:

[1] K. E. Bean, "Anisotropic Etching of Silicon" *IEEE Transactions on Electron Devices* UED-25 (1978) No. 10, pp. 1185-93
[2] U.S. Pat. No. 3,397,278 (Pomerantz)
[3] FI Pat. No. 48,229 (Suntola).

OBJECT AND SUMMARY OF THE INVENTION

The object of the present invention is to provide a capacitive humidity sensor which meets all of the above requirements a, b and c, as well as a method for the manufacture of such a sensor.

The invention is based on the idea that the first bottom electrode is connected to the sensor surface by means of conductive structures expanding from the support base outwards so that only small slots remain between the top edges of these structures and that the active layer remains in the hollow space formed by adjoining structures.

More specifically, the capacitive humidity sensor in accordance with the invention is characterized in what is stated in the characterizing part of claim 1.

On the other hand, the method for the manufacture of the humidity sensor is characterized in what is stated in the characterizing part of claim 6.

By means of the invention, remarkable advantages are obtained. Thus, the sensor in accordance with the invention meets all of the requirements a, b and c mentioned above. Nor is it sensitive to touching. Moreover, its handling is easy.

BRIEF DESCRIPTION OF THE DRAWINGS

The invention will be examined in the following in more detail by means of the exemplifying embodiments shown in FIGS. 3 to 13 in the attached drawing.

DETAILED DESCRIPTION OF THE INVENTION

Figure 1:
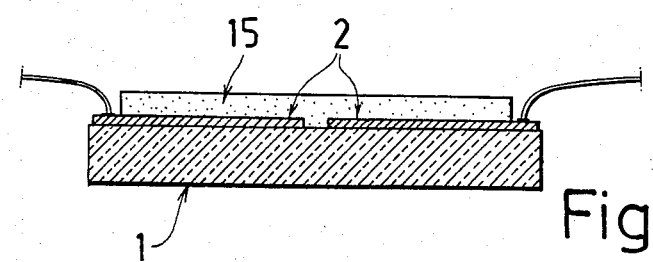
FIGS. 1 and 2 are cross-sectional views of prior art capacitance humidity sensors.
Figure 2:
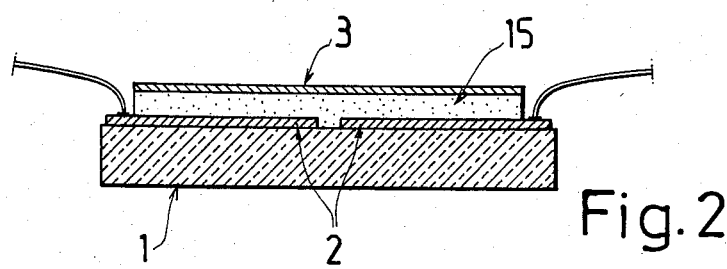
Figure 3:
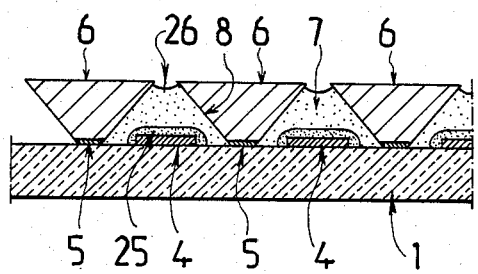
FIG. 3 is a cross-sectional view of a sensor in accordance with the invention.
Figure 5:
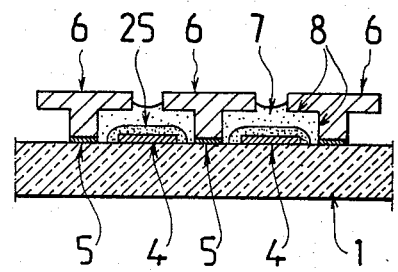
FIG. 5 is a cross-sectional view of a second sensor in accordance with the invention.
Figure 4:
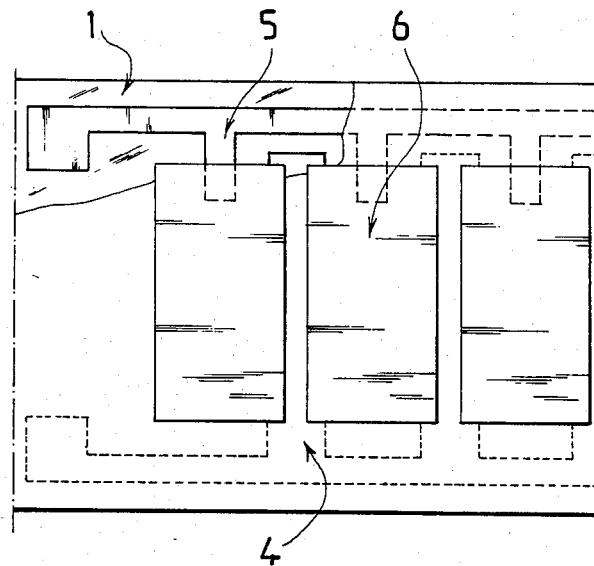
FIG. 4 shows the sensor in accordance with FIG. 3 as viewed from above.
Figure 6:
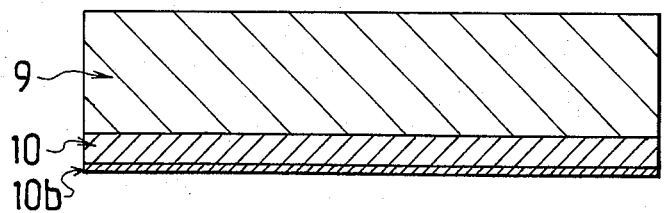
FIGS. 6 to 12 illustrate the manufacture of a sensor of the type shown in FIGS. 3 and 4, step by step.
Figure 7:
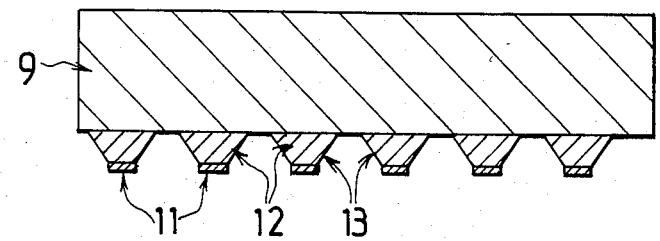
Figure 8:
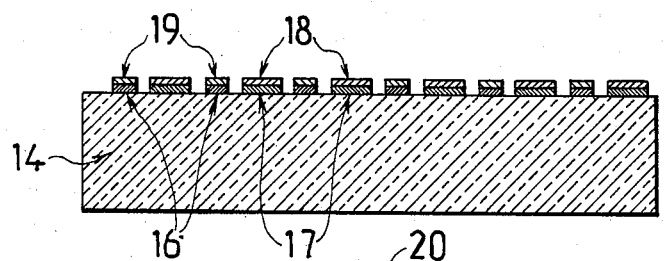
Figure 9:
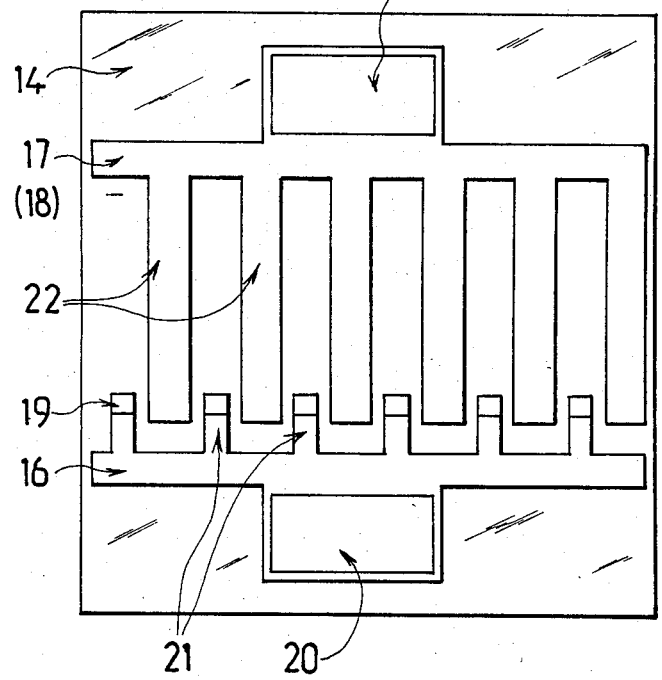
Figure 10:
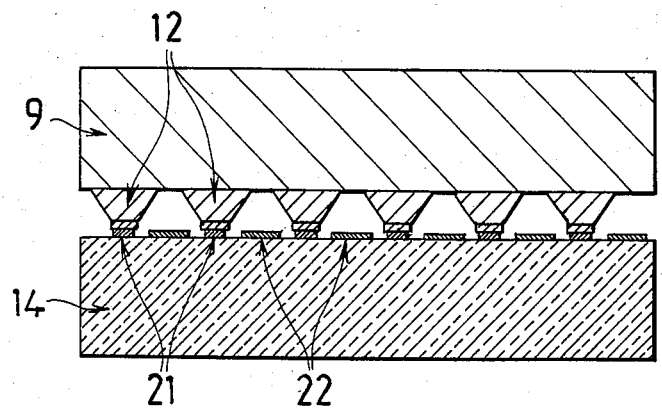

The capacitive humidity sensor shown in FIGS. 3 and 4 has electrode patterns 4 and 5 on a glass substrate 1. The electrodes are of a chemically resistant metal (e.g., Pt, Pd, Ta, Au), and they are protected by a thin isolator film 25 (e.g., $Ta_2O_5$, $Si_3N_4$, $SiO_2$, etc.). The metal pattern 5 creates an electrical contact with the beams 6, which are of trapezoidal section. They are made of silicon, metal, or of some other conductive material and are fixed to the substrate 1. Between the top portions of the beams 6, there is a narrow (e.g., about 1 $\mu$m) slot 26. Between the beams 6, there is an insulator material sensitive to humidity, e.g. an appropriately selected polymer 7. The capacitance sensitive to humidity is formed between the metal areas 4 and the side walls 8 of the beams 6.

The construction described can be manufactured, e.g., as follows (FIGS. 6 to 12):

An epitactic layer 10 weakly doped with boron (N lower than $10^{17}$ 1/cm$^3$) is deposited on a (100)-directional silicon disc 9 strongly doped with boron (N higher than $10^{17}$ 1/cm$^3$). The surface of the layer 10 is doped strongly with boron (N higher than $10^{20}$ 1/cm$^3$). The thickness of the doped surface layer 10b is about 1 $\mu$m. Into the layer 10b, areas 11 are patterned photolithographically in which the surface layer is retained (from the remaining areas, it is etched off by means of an etching agent which is selective in respect of strongly doped silicon). When the layer 10 is etched in an appropriate etching agent 1 (e.g., KOH), beams 12 with diagonal edges and of a thickness equal to the thickness of the layer 10 are obtained at the areas 11. The sides 13 of the beams 12 are parallel to the crystal plane (111) and form an angle of 54.74° with the face of the disc.

Onto the glass substrate 14, a thin metal film was deposited by means of prior art methods, which metal film was photolithographically patterned to form areas 16 and 17. Onto the areas 16 and 17, it was possible to form an isolator film 18, e.g. by anodically oxidizing the metal film, as well as contact areas 19 and 20 of a different metal, which areas can be omitted if the soldering quality of the metal film is good and it makes a good contact with p+ —Si (silicon strongly doped with boron).

The substrate 14 and the silicon disc 9 are placed against each other so that the fingers 21 on the metal area 16 (FIGS. 9 and 10) reach contact with the beams 12 on the silicon disc and the fingers 22 on the area 17 become placed between the beams 12 without reaching contact with them. In this position, the glass substrate and the silicon disc 9 are joined together by means of the method described in the cited publication No. 2. The faces of the beams 12 form a chemical bond with the substrate 14. Hereinafter, the silicon disc 9 is etched off by means of an etching agent which etches the strongly doped area but not the weakly doped beams 12.

Figure 11:
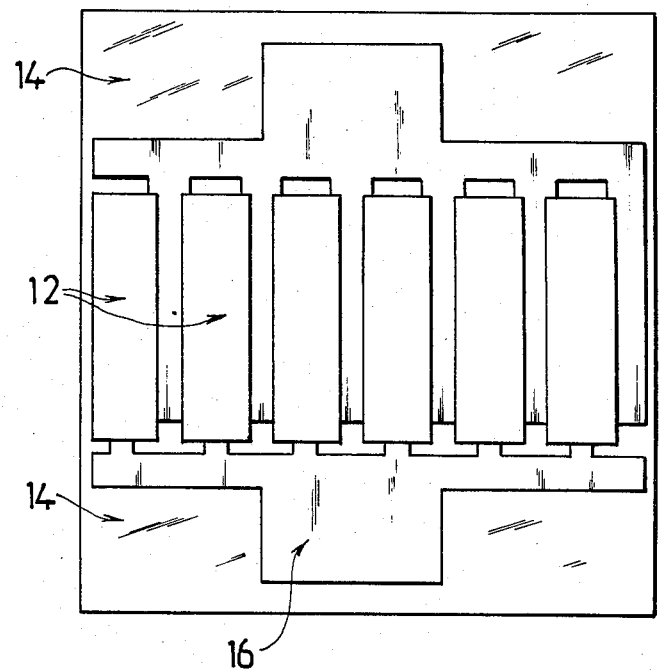
Figure 12:
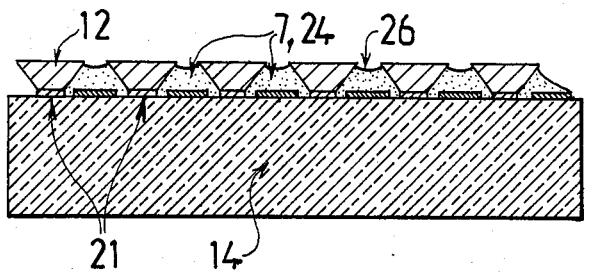
Figure 13:
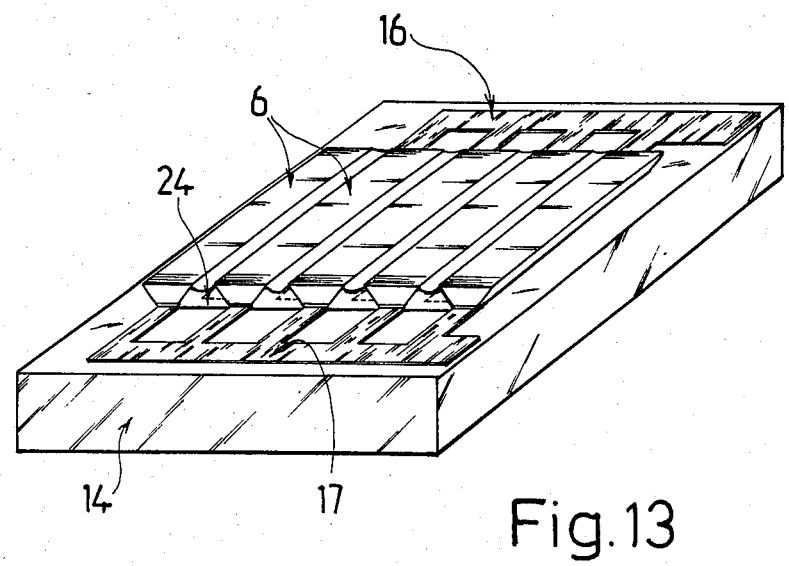
FIG. 13 is an axonometric view of a complete sensor in accordance with the invention.

The construction in accordance with FIGS. 11 and 12, wherein the beams 12 adhere firmly to the substrate glass 14 and form an electrical contact with the fingers 21 on the metal area 16, is submerged into a solution of a polymer sensitive to humidity. The solution penetrates into the space 24 between the beams 12. The construction is lifted off out of the solution and the solvent of the polymer is allowed to evaporate, whereby a solid polymer remains in the space 24.

Within the scope of the invention, it is also possible to conceive solutions differing from the exemplifying embodiment described above. Thus, the beam structures 6 may also be, e.g., of T-section in the way shown in FIG. 4. The essential feature is that a narrow slot remains between the top faces of adjoining beam structures 6.

What is claimed is:

1. Capacitive humidity sensor, which comprises
   a substrate made, e.g., of glass,
   at least one first and one second bottom electrode arranged close to each other on the substrate,
   an active layer, which fills the area between the first and the second bottom electrode on the substrate and extends to above the top face of the second electrode,
   a plurality of conductive, beam-shaped structures placed side by side, connected to the first electrode, and having an upwardly widening cross-section, said structures limiting portions of the active layer between themselves from two sides such that a narrow slot is formed between the top faces of said structures.

2. Humidity sensor as claimed in claim 1, wherein the beam-shaped structures are at least substantially of a trapezoidal cross-sectional form.

3. Humidity sensor as claimed in claim 1, wherein the beam-shaped structures are at least substantially of a T-shaped cross-sectional form.

4. Humidity sensor as claimed in claim 1, wherein the beam-shaped structures are made of silicon.

5. Humidity sensor as claimed in claim 1, wherein the beam-shaped structures are made of a metal.

6. Method for the manufacture of a capacitive humidity sensor as claimed in claim 1, comprising:
   (a) depositing an epitactic layer weakly doped with boron onto a silicon disc or equivalent,
   (b) doping the surface of the layer strongly with boron so as to form a surface layer,
   (c) patterning, e.g., photolithographically, into this surface layer such oblong areas as are to be retained,
   (d) etching off by means of an appropriate etching agent, e.g. KOH, the areas between the desired areas so that adjoining ridges projecting outwards from the silicon disc are formed,
   (e) depositing onto a substrate, e.g., a glass substrate, at least one first and one second electrode layer as thin metal films,
   (f) fitting the substrate and the silicon disc against each other so that the ridges and the first electrode reach contact with each other, and joining them together in a way known per se,
   (g) etching off the silicon disc by means of an etching agent which etches the strongly doped silicon material such that only the ridges remain as beam-shaped structures,
   (h) submerging the construction in this way obtained into a solution of an active isolating material sensitive to humidity, e.g., a polymer, and allowing this solution to penetrate into the space between the beams, and
   (i) lifting off the construction out of the solution, and allowing the solvent to evaporate, whereby a solid active isolator material remains in the space between the beams.

* * * * *